(12) United States Patent
Kahraman et al.

(10) Patent No.: US 11,344,477 B2
(45) Date of Patent: May 31, 2022

(54) SYNCHRONIZED MEDICATION TRACKING SYSTEM

(71) Applicant: Istanbul Üniversitesi Rektörlüğü, Fatih/Istanbul (TR)

(72) Inventors: Mustafa Kahraman, Fatih/Istanbul (TR); Mehmet Akif Karan, Istanbul (TR)

(73) Assignee: Istanbul Üniversitesi Rektörlüğü, Fatih/Istanbul (TR)

( * ) Notice: Subject to any disclaimer, the term of this patent is extended or adjusted under 35 U.S.C. 154(b) by 26 days.

(21) Appl. No.: 16/968,135

(22) PCT Filed: Feb. 8, 2019

(86) PCT No.: PCT/TR2019/050078
§ 371 (c)(1),
(2) Date: Aug. 6, 2020

(87) PCT Pub. No.: WO2020/022985
PCT Pub. Date: Jan. 30, 2020

(65) Prior Publication Data
US 2021/0369570 A1 Dec. 2, 2021

(30) Foreign Application Priority Data
Feb. 8, 2018 (TR) ................................ 201801762

(51) Int. Cl.
*G16H 20/13* (2018.01)
*A61J 7/04* (2006.01)
(Continued)

(52) U.S. Cl.
CPC .......... *A61J 7/0427* (2015.05); *A61J 7/0084* (2013.01); *G07F 17/0092* (2013.01);
(Continued)

(58) Field of Classification Search
CPC ........................... G07F 17/0092; G06H 20/13
See application file for complete search history.

(56) References Cited

U.S. PATENT DOCUMENTS 5,509,573 A * 4/1996 Campoli ................ A61C 19/00
221/133
8,145,353 B1 * 3/2012 Cotner ................ G07F 17/0092
700/241
(Continued)

FOREIGN PATENT DOCUMENTS

CN 101999988 A 4/2011
WO 2020022985 A3 1/2020

*Primary Examiner* — Timothy R Waggoner
(74) *Attorney, Agent, or Firm* — Rahman LLC

(57) ABSTRACT

It is vital to use the right medicine at the right time, at the right dose while taking medicines; forgetting to take medicines is a problem seen in patients with forgetfulness or carelessness, especially elderly patients, and in patients who are on continuous medication and/or have to use a medicine for a certain period. The synchronized medication tracking system of the present invention is designed to solve the problems of the patients. The present invention includes a cartridge that can be carried on patients at all times, a filling device for placing the medicines in portable cartridges, and an application to allow tracking this information.

12 Claims, 7 Drawing Sheets

(51) Int. Cl.
*G16H 40/67* (2018.01)
*A61J 7/00* (2006.01)
*G07F 17/00* (2006.01)

(52) U.S. Cl.
CPC ............ *G16H 20/13* (2018.01); *G16H 40/67* (2018.01); *A61J 2200/30* (2013.01); *A61J 2200/70* (2013.01)

(56) References Cited

U.S. PATENT DOCUMENTS

| | | | |
|---|---|---|---|
| 9,245,093 B2* | 1/2016 | Shaw | G16H 20/13 |
| 9,475,633 B2* | 10/2016 | Hoover | G16H 20/13 |
| 9,589,412 B2* | 3/2017 | Shimmerlik | B60P 3/0257 |
| 10,456,332 B2* | 10/2019 | Paz | A61J 1/03 |
| 2009/0281657 A1* | 11/2009 | Gak | G16H 20/13 |
| | | | 700/242 |
| 2012/0259456 A1* | 10/2012 | Saltsov | A61J 7/0084 |
| | | | 700/236 |
| 2015/0359711 A1* | 12/2015 | Ducatt | A61J 7/0076 |
| | | | 221/13 |
| 2017/0354573 A1 | 12/2017 | Lee et al. | |
| 2018/0012439 A1 | 1/2018 | King et al. | |

* cited by examiner

SYNCHRONIZED MEDICATION TRACKING SYSTEM

TECHNICAL FIELD

It is vital to use the right medicine at the right time, at the right dose while taking medicines; forgetting to take medicines is a problem seen in patients with forgetfulness or carelessness, especially elderly patients, and in patients who are on continuous medication and/or have to use a medicine for a certain period. The synchronized medication tracking system of the present invention is designed to solve the problems of the patients.

STATE OF ART

To solve the medication use and dosage amount forgetfulness problems, simple drug boxes can be prepared weekly, ten-day, etc. for daily or one-time (such as morning-evening) use. When the wrong pills are placed in the wrong boxes, it is not possible to correct the errors as they are also removed from their packaging.

Alarm systems can be added to these boxes according to drug usage hours; these zo alarms are only detectable by the patient or the caregiver when they are near the medication box. If the patient's relatives are away, the alarm cannot receive the warning, so they cannot be informed. In addition, although it can be written on the boxes whether the medication is to be taken on an empty or a full stomach, this creates a problem especially for elderly patients with reading problems. Robotic systems created for drug distribution and used in large pharmacies are involved in delivering drugs to patients. These computer-aided systems do not include personalized approaches.

DESCRIPTION OF THE INVENTION

The present invention relates to a synchronized medication tracking system to eliminate the aforementioned drawbacks and provide new advantages to the relevant technical field. The present invention comprises a cartridge that can be carried on patients at all times, a filling device for placing the medicines in portable cartridges, and an application to allow tracking this information.

The object of the invention is to provide a system to meet and follow-up individual patient needs and monitor.

With the system of the invention, it is ensured that the following measures are taken against the problems that may occur during medical treatments:
  Confirming the accuracy of the medications the patient takes
  Ensuring that the patient takes the medication on time
  Ensuring that the patient takes the correct dose of medication
  Ensuring that the medication is refilled before it runs low thanks to the warning system
  Monitoring of the medication taken from the records
  Ensuring that relatives can intervene or have information when necessary

DRAWINGS

Embodiments of the present invention briefly summarized above and discussed in more detail below can be understood by reference to the exemplary embodiments described in the accompanying drawings. It should be noted, however, that the accompanying drawings only illustrate the typical structures of the present invention and therefore, they will are not intended to limit the scope of the invention, since it may allow other equally effective structures.

Identical reference numbers are used where possible to identify identical elements common in the figures to facilitate understanding. The figures are not drawn with a scale and can be simplified for clarity. It is contemplated that the elements and features of an embodiment may be usefully incorporated into other embodiments without further explanation.

DESCRIPTION OF THE DETAILS IN THE DRAWINGS

Figure 1:
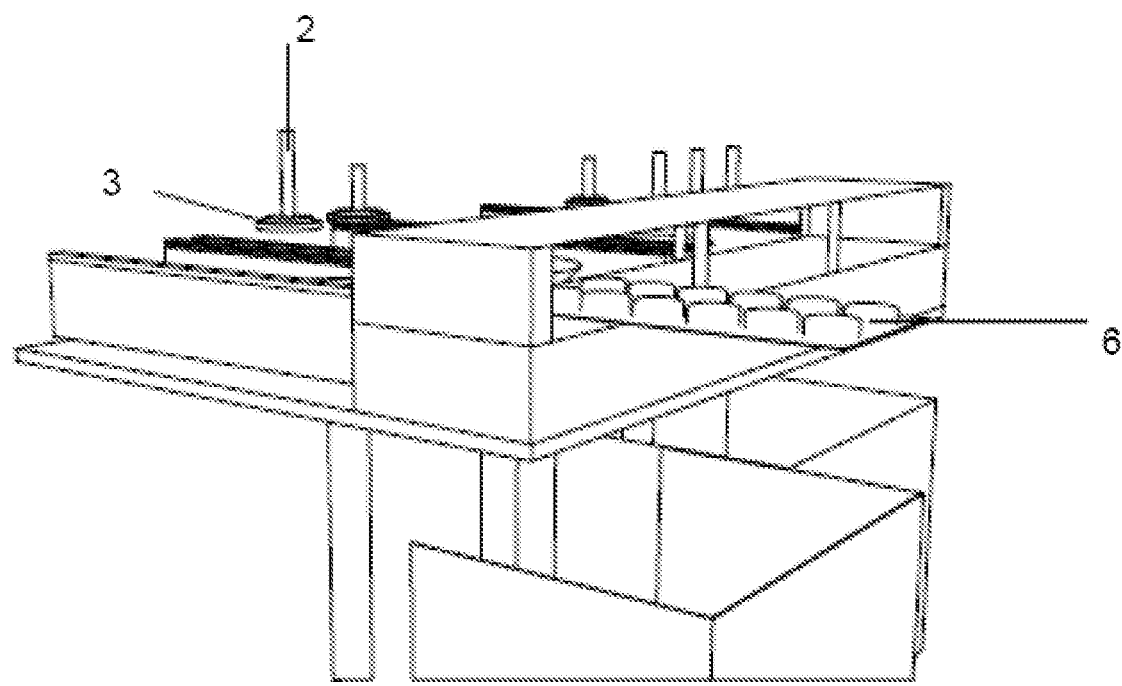
FIG. 1 is a representative view of the filling device with the top and side covers removed.

The equivalents of the reference codes shown in the figures are provided below.
1—Filling device,
2—Tablet extraction lever,
3—Pressure base,
4—Breaker arm
5—Knife,
6—Medication packaging,
7—Tablet
8—Funnel,
9—Tube,
10—Lever,
11—Cartridge path,
12—Cartridge outlet,
13—Screen,
14—Lever path,
15—Tube chamber,
16—Tube housing,
17—Tube spring,
18—Medication extraction part,
19—Wing,
19a—Retaining wings,
20—Cartridge,
21—Tube area,
22—Processor,
23—Battery,
24—Buttons,
25—Cartridge screen,
26—Medicine outlet,
27—Medicine outlet cover,
28—Motor,
101—Prescription recognition stage, 102—Medicine recognition stage,
103—Medicine administration stage,
104—Medicine comparison stage,
105—Inserting the cartridge into the device,
106—Inserting the tubes into the device,
107—Taking the tablets out of the package,
108—Placing the medicines into tubes,
109—Tube-tablet pairing,
110—Medication filling phase,
111—Inserting the tubes into the cartridge,
112—Transferring information from the device to the cartridge,
113—Application-cartridge pairing,
114—Providing data access,
115—Delivery of the cartridge to the patient.

DETAILED DESCRIPTION OF THE INVENTION

In this detailed description, preferred alternatives of synchronized medication tracking system embodiment of the invention are described only for a better understanding of the subject and without any limiting effect.

The invention has been realized by forming and combining 3 different elements. These elements are medication filling device (1), user-specific cartridge (20) housing the medication, filling device (1), and an application software providing synchronization between cartridge (20) and the system with the data transfer. This software also connects to a public server to exchange information.

The first element of the invention, the filling device (1), is loads the medication into the cartridge (20) with zero-touch according to the patient's prescription and completes the synchronization chain in the system since it communicates with the system.

The patient's prescription is entered from the screen (13) in the filling device (1). This entry can also be made with the TR ID. Numbers of the patients is similar to that of the general health system. After the prescription is entered, the automatic loading of the medication into the cartridge (20) in the filling device (1) with zero-touch and additionally the information such as the medication and their administration times, the dosages and the administration conditions along with the patient and patient relative information is entered. This information is required for the functions such as warning the patient and the patient relatives on the administration time of the medication and warning the patient and patient relatives if the medication is not taken. The regulation of the medication according to the prescription is performed by reading the QR code or bar code of the medication to the QR code and bar code readers contained in the filling device (1). As an alternative to the QR code and bar code readers, the identification of the medication can be performed using a camera.

In the filling device (1), as shown in FIG. 1, when the patient's prescription is loaded into the system, the cartridge (20) is received in the filling device (1) and the cover of the cartridge (20) is opened. The prescription medicines are applied to the filling device (1)r in their medication packages (6). As the medication package (6) proceeds in the medication extraction part, the sensors detect this progress and notifies the device processor. The processor, which evaluates this information, commands the tablet extraction levers (2) to apply pressure. The pressure bases (3) on the underside of the tablet extraction on levers (2) apply pressure to the tablet medication package (6) so that the tablet ejects from the package without any damages and falls into the funnel (8). This process is applied to the entire medication package (6) provided that it is in accordance with the prescription. Alternatively, in the extraction process, the tablet is removed from the packaging by applying heat or cutting.

The processor displays on screen (13) which medicines have been extracted and the quantity. In the filling device (1), multiple simultaneous medicine extraction processes are possible with a medication extraction part (18) in variable numbers according to the size of the filling device (1). The medication extraction part (18) has portable wings (19) which come closer and move away from each other and are equipped with retainer wings (19a) on the upper part so as to empty the medicine package. In the filling device (1), the breaker arm (4) equipped with a knife 2 at the end is used to prepare the desired dosage by cutting the tablet in half when the prescription medication is entered in half a tablet size. The tablet (7) taken with the medicine division process as entered when the prescription is defined is divided into two parts with the breaker arm (4) equipped with the knife (5) cutting and transferred to the tube 9 in 2 parts. Furthermore, in the present invention, the tablets (7) to be loaded into the cartridge (20) can be taken into the tube 9 by cutting one by one without removing them from the medication package (6) or can be loaded into a cartridge (20) which can be designed as a chamber.

Figure 7:
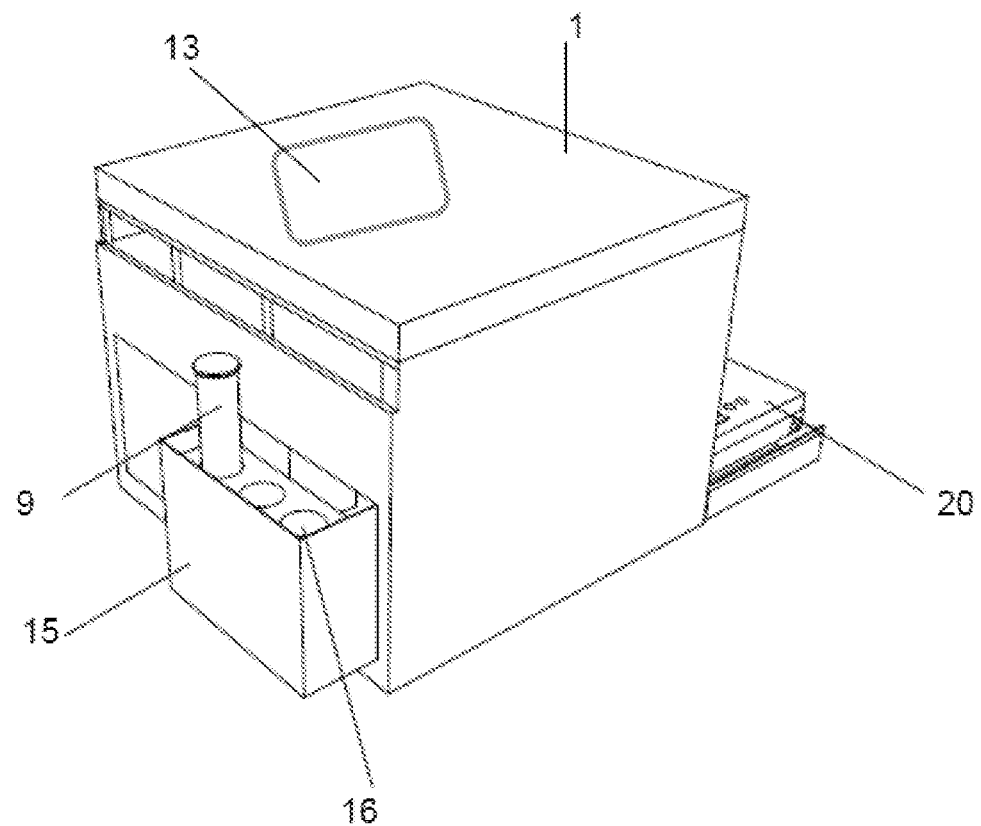
FIG. 7 is a perspective view of the filling device.
Figure 8:
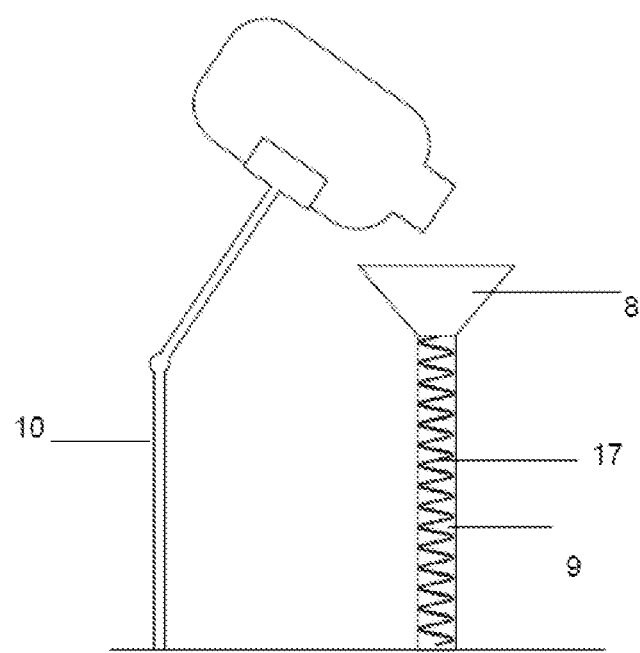
FIG. 8 is a representative view of the lever and the filling state within the filling device.

As shown in FIG. 7, on one side of the filling device (1), there is a tube chamber (15), which is opened like a drawer, in which the tubes 9 are inserted into the tube housings (16). The tubes 9 placed there are transferred to the funnels (8) and to the cartridges (20) by means of the levers (10) for receiving the medicine. In the filling device (1), as shown in FIG. 8, the levers (10) are also used for transferring the medicines sold in bottle type or cylindrical boxes to the tubes 9. The medicine bottle coming to the medication extraction part (18) is grasped by the lever (10) and poured into the funnel (8) and the medication tablets are transferred to the tube 9.

Figure 2:
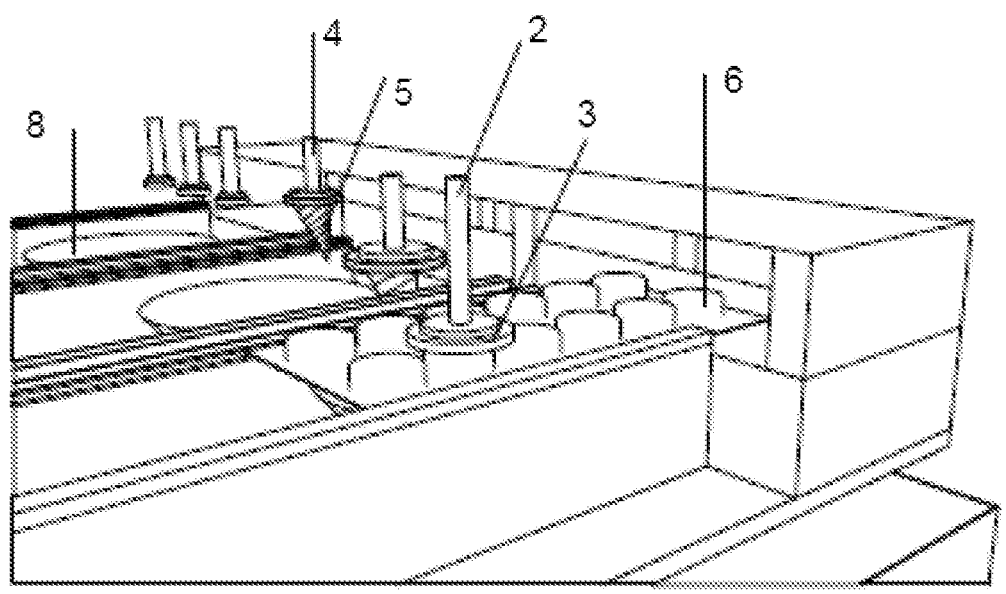
FIG. 2 is a side view of the filling device with the top cover removed.
Figure 3:
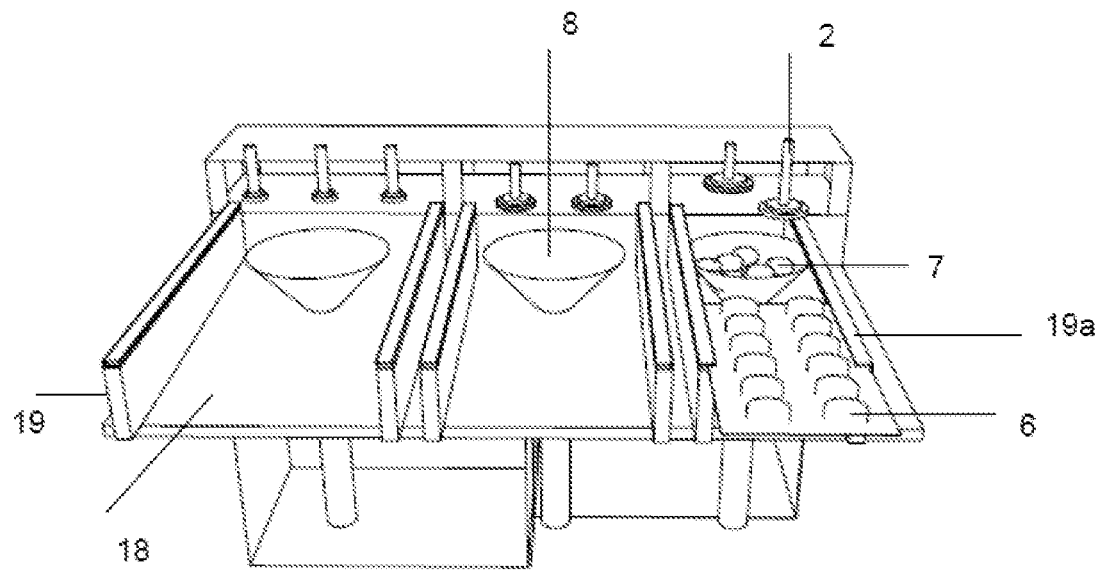
FIG. 3 is a representative view of the tablet extraction system in the filling device.
Figure 4:
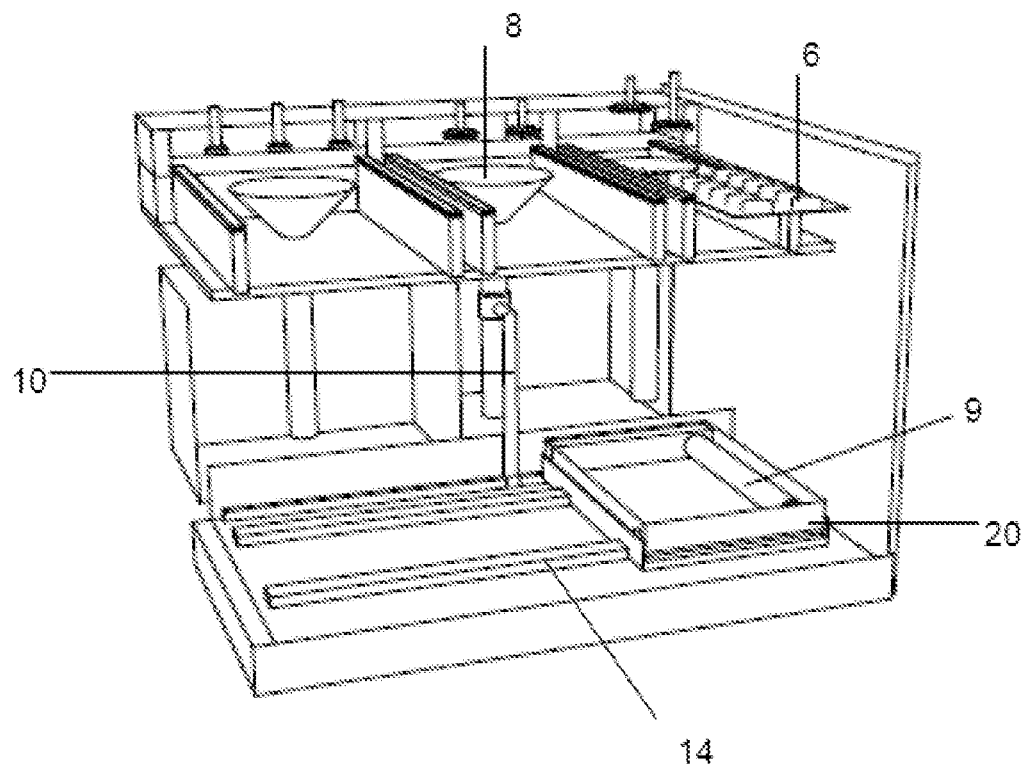
FIG. 4 is a representative view of the filling device with the top, side and back covers removed.
Figure 5:
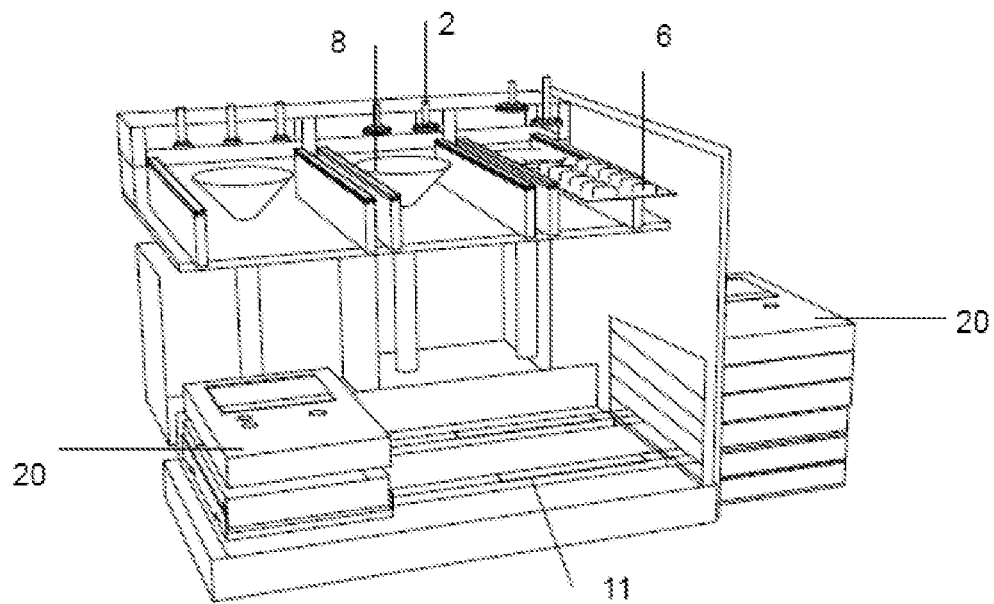
FIG. 5 is the state of the cartridge in the filling device.
Figure 6:
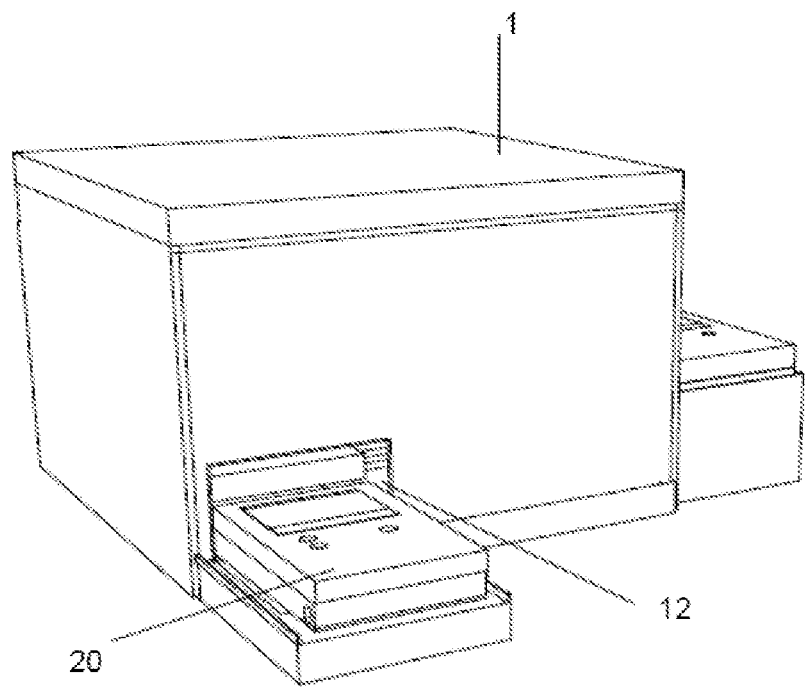
FIG. 6 shows the exit of the cartridge from the filling device.

In the filling device (1), as shown in FIG. 2, the extracted tablets fall into the funnel (8) and pass into the tube 9 to which the narrow mouth of the funnel (8) is connected. When the loading is complete, the tubes 9 are separated from the funnel (8) by a robotic lever (10) and placed in the tube area (21) on the cartridge (20). While the movement of the lever (10) is performed by a programmable software, it performs the left and right movement within the filling device (1) through the lever path (14). The number of levers (10) in the filling device (1) can be increased. After the tubes 9 with medication are inserted into the cartridge (20), the cover of the cartridge (20) is closed and it exits from the cartridge outlet (12) through the cartridge path (11) in the form of a movable band. In this process, the prescription and patient information is loaded into the processor (22) of the cartridge (20) by wireless data transfer (Bluetooth, Wi-Fi, infrared, RFID, GSM, etc.) and made available to the patient.

Figure 9:
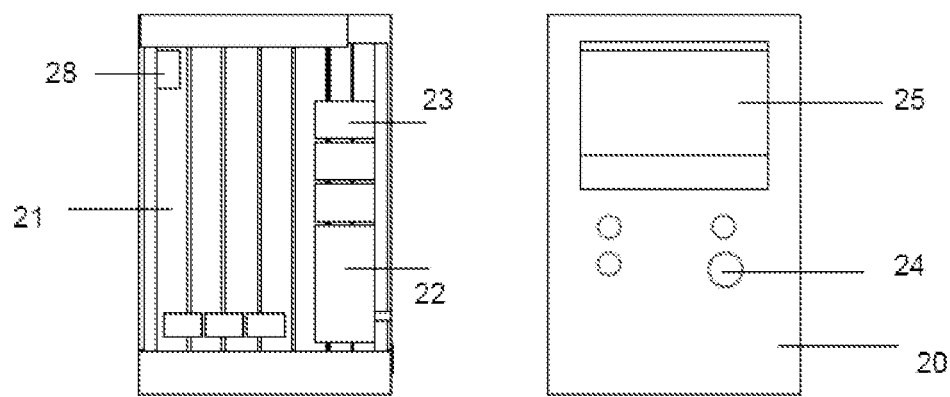
FIG. 9 is a representative view of the interior of the cartridge and is a general view.

The second element constituting the system, the cartridge (20), as shown in FIG. 9, contains a tube area (21), a rechargeable battery (23) providing power to the cartridge, the motor (28) providing movement to the tubes 9, a processor (22), a touch cartridge screen (25) displaying information on the front side, and buttons (24) for functions such as turning it on/off and sound control.

Figure 10:
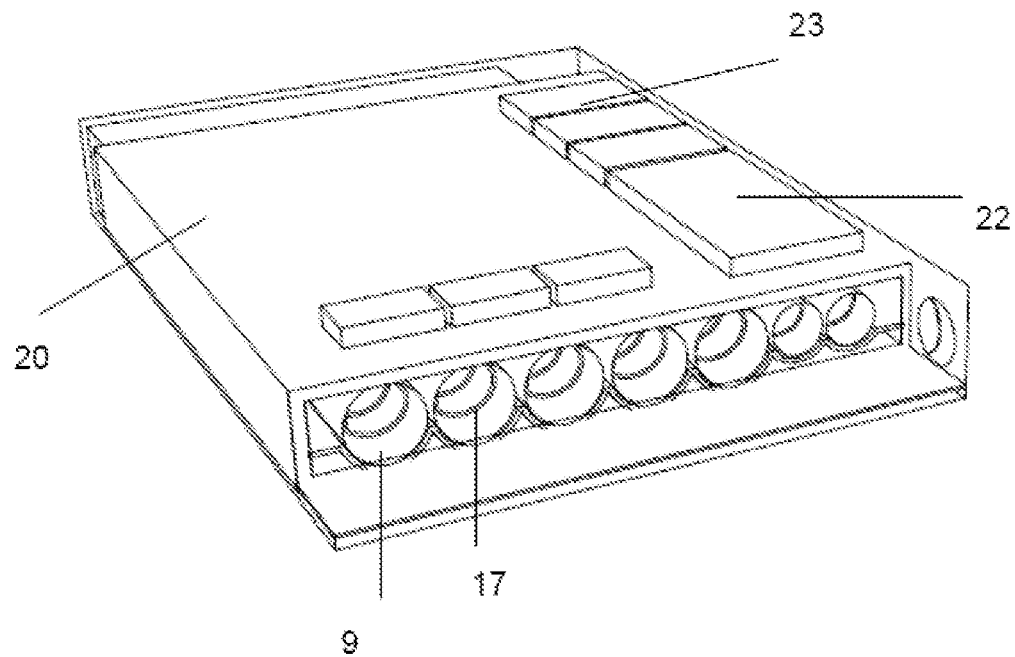
FIG. 10 is a representative perspective view of the interior of the cartridge.
Figure 11:
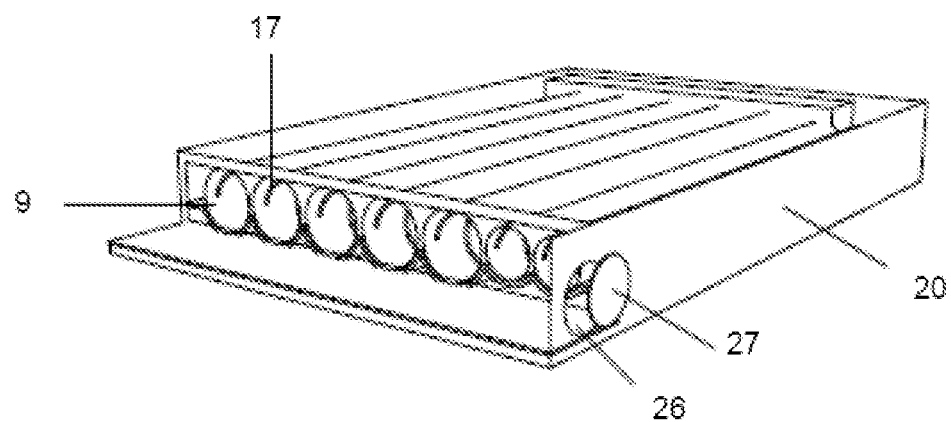
FIG. 11 is a representative view of the cartridge with the cover removed.
Figure 12:
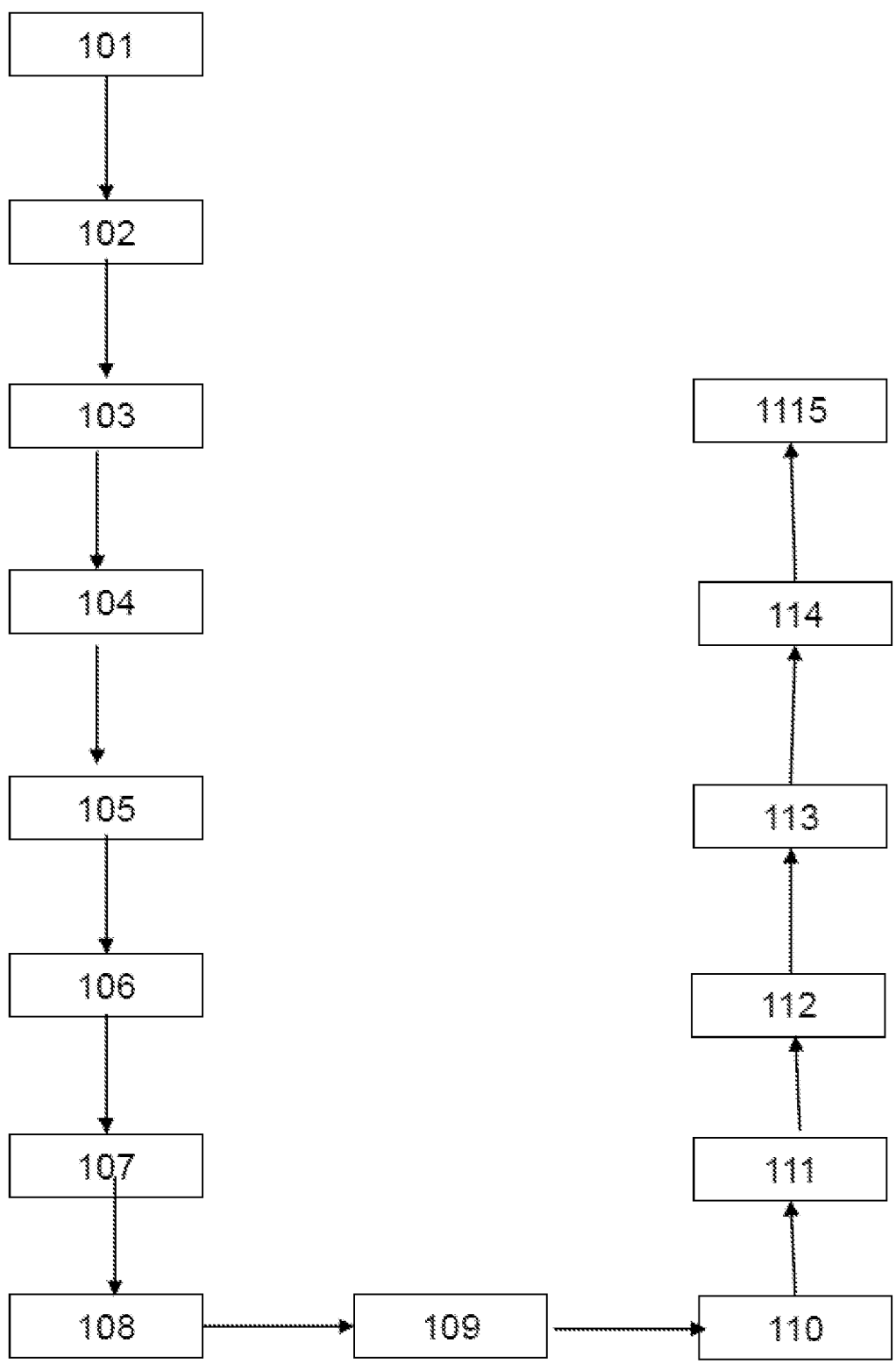
FIG. 12 is a work flow chart of the system.

In the cartridge (20), as shown in FIG. 10, a spiral tube spring (17) is used to ensure the one-by-one extraction of the medicines in the tubes 9 from the tubes 9 placed in the tube area (21) one by one according to the dosage. With the rotation taken from the motor (28), these tube springs (17) extracts one tablet placed between the spirals from the tube 9 in each rotation, and as shown in FIG. 11, the medicine outlet cover (27) opens and allows the medicine to exit from the medicine outlet (26) to the patient's use. As an alternative to the exit of the tablet from the tube 9, the process may be performed by applying a conveyor belt which is made of flexible material on the inner surface of the tube 9, which will be mutually applied to the upper and lower sides, with small plies spaced apart therebetween. The tablets placed between the wings on the belt move with the movement of the tape, one tablet at a time. When the wings are on the side of the tube 9 surface, the wings are bent between the inner surface of the tube 9 and the tape to enable movement of the tape. In addition to these embodiments, as a further alternative, medicine extraction can be performed by a spring of the kind used in the chargers in the tubes 9 and a plate between the spring and the tablet.

The processor (22) of the cartridge performs the functions such as informing the patient relative and/or health care provider about the loaded prescription and patient information, medication administration times and warning alarms, whether the patient has taken the medication, activation of the motor (28) for the release of the medicine from the tube 9, operation of the functional buttons (24), displaying the information and statuses on the display cartridge screen (25). The battery (23) provides the power in the cartridge (20) and this battery (23) is replaceable and rechargeable.

The present invention comprises a cartridge (20) that can be carried on patients at all times, a filling device (1) for placing the medicines in portable cartridges (20), and an application to allow tracking this information.

The cartridge (20) provides accurate, regular and medication usage to the patient by specifying the day, the time, the empty/full stomach state for the administration of the medication thanks to the time-calendar application and can be synchronized with the mobile application of the patient and the patient's relative. When it is time for the medication to be taken by the patient, both the cartridge (20) gives an audible and visual warning and the mobile application sounds an alarm and the patient is warned by a double alarm method. If the patient does not hear or ignore the warnings, the application sends a warning message to the patient's relatives and informs them. Once the patient has received the warning, the pills are extracted from the tube 9 by pressing on the touch cartridge screen (25) or normal buttons (24) on the cartridge (20). The patient opens the medication outlet cover and receives the medication by pressing a button (24) again to receive the medication from the medicine outlet (26) in the cartridge (20). The tube 9 parts of the cartridge (20) are equipped with sensors to answers questions such as "When the patient pressed the button (24), did the pills come out of the tubes 9? If so, was the patient able to take the pill when the second key button (24) was pressed?" etc. These sensors will detect the medicine and inform the system. In addition, information such as the quantity of the medication taken and the time of administration can be obtained and stored in memory and can be shared with relevant people.

The third component of the system, the application, performs actions and processes such as the exchange of information between the filling device (1), the cartridge (20), the patient, the patient relatives, health care providers and the general health system, the synchronization between them, the storage and sharing of information such as medicine administration times, medicine use etc. Furthermore, the application gives an alert when the medicine in the cartridge (20) runs low and warns and informs the relevant people when the medicine is not taken in time by the patient. In terms of patient use of the system, the application is installed on the smartphones of both the patient and the patient's relative, if necessary. In the application, the user profile is created and it is operated by logging in with the user name and password. The patient relatives who wish to share medicine use data may also use the same application. This information is also monitored on a central server and can be displayed on the doctors' computers.

The operation phases of the process are as follows:

a—Filling the medication in blister packs into tubes 9,

1. The person to use the filling device (1) enters the medication usage instructions and medication information that the patient needs into the system. This is the prescription recognition stage (101).

2. The bar code on the medicine box is read into the filling device (1) and filling device (1) recognizes the medication. This step is the medicine recognition stage (102).

3. The medicine packages (6) are removed from the box and placed in the medication extraction parts (18) in filling device (1). This step is the medicine administration stage (103).

4. The filling device (1) detects the medication package (6) and compares the medicine comparison stage (104) with the QR code-bar code read or camera. The comparison result:

a. In case of medicine-bar code match, the process continues.

b. In the absence of a medicine-bar code match, the process is stopped. It warns the user of the filling device (1) to check.

5. The cartridge (20) is inserting the cartridge into the device (105).

6. The tubes (9) into which the medication is placed are placed in the tube housings (16) located in the tube chamber (15) in inserting the tubes into the device (1) (106).

7. If there is a medicine-bar code match, the medicine is removed from the package by pressure or using other alternative methods described taking the tablets out of the package (107).

8. The pills are taken into the funnel (8) and placing the medicines into tubes (9) (108).

9. The size of the tubes (9) is matched with the size of the pills. The processor of the filling device (1) determines which size of the medicine is placed in which tube. This step is the tube (9)-tablet (7) pairing (109).

10. In the filling device (1), the processor is pre-loaded with information about the dimensions of each medicine. Thus, each medicine can be filled into different tubes (9) according to its size. This step is the medication filling phase (110).

11. The tubes (9) filled with pills in the filling device (1) are placed in inserting the tubes into the cartridge (20) (111).

12. While the cartridges (20) are filled with medicine-containing tubes (9), the information such as which tube (9) contains which medicine, the administration frequency and time of the medicine, whether the medicine will be taken on an empty or full stomach are loaded on the processor (22) in transferring information from the device to the cartridge (20) (112).

13. The medication information in filling device (1) is sent to the application in the patient's phone via SMS, Bluetooth, etc. The user will be prompted to accept this information. Thus, the application in the patient phone and the drug transport cartridge (20) are connected to each other application-cartridge pairing (113).

14. The device may contain Wi-fi, GSM module, Bluetooth module, RFID, etc. modules. Remote data access is provided with these modules (114).

15. After filling, the cartridge (20) is removed from the filling device (1) and delivery of the cartridge to the patient (115).

The invention claimed is:

1. A synchronized medication tracking system comprising:
a filling device comprising a tablet extraction lever; a pressure base; a breaker arm; a knife; a medication packaging; a funnel; a tube; a lever; a cartridge path; a cartridge outlet; a screen; a lever path; a tube chamber; a tube housing; a tube spring: a medication extraction part; a wing; and retaining wings;
a cartridge;
application software; and
a central server.

2. The synchronized medication tracking system according to claim 1, wherein a prescription of a patient is entered in the screen with a patient TR ID. No., the cartridge is received by the filling device and a top cover of the cartridge is opened, a medication is applied to the filling device in the medication packaging, as the medication packaging proceeds towards the medication extraction part, sensors detect this and inform a device processor and upon a command to apply pressure to the tablet extraction lever by the device processor, the pressure base located on lower portions of the tablet extraction lever apply pressure to the tablet medication packaging and a tablet is dropped inside the funnel after being taken out of the medication packaging without harming the tablet.

3. The synchronized medication tracking system according to claim 1, wherein the medication extraction part has portable wings which come closer and move away from each other and are equipped with the retaining wings on an upper part so as to empty the medication packaging, the device processor displays on the screen which medicines have been extracted and the quantity, in the filling device, multiple simultaneous medicine extraction process are possible with the medication extraction part in variable numbers according to the size of the filling device.

4. The synchronized medication tracking system according to claim 1, wherein the breaker arm is equipped with the knife at an end, which is used to prepare a desired dosage by cutting a tablet in half when prescription medication is entered in half a tablet size.

5. The synchronized medication tracking system according to claim 1, wherein the tube chamber is opened so that the tube is inserted into the tube housing, tube placed there is transferred to the funnel and to the cartridge by means of the lever for receiving the medicine, for the transfer of the medicines provided in bottle type or cylindrical boxes to the tube, and wherein the lever is used with a certain angle and vibration to grab a bottle coming to the medication extraction part.

6. The synchronized medication tracking system according to claim 1, wherein the tube loaded with a tablet is separated from the funnel by a robotic lever and placed in the tube area on the cartridge, while the movement of the robotic lever is performed by programmable software; it performs a left and right movement within the filling device through the lever path, a number of robotic levers can be increased, after the tube with medication is inserted into the cartridge, the cover of the cartridge is closed and it exits from the cartridge outlet through the cartridge path in the form of a movable band.

7. The synchronized medication tracking system according to claim 1, wherein prescription and patient information is loaded into a processor of the cartridge by wireless data transfer by a processor of the filling device.

8. The synchronized medication tracking system according to claim 1, wherein the cartridge comprises:
a tube area;
a processor;
a battery;
buttons;
a cartridge screen;
a medicine outlet;
a medicine outlet cover; and
a motor.

9. The synchronized medication tracking system according to claim 8, wherein the processor stores and transmits medication use information, actuates the motor to release the medication from the tube, operates the buttons, displays the information and statuses on the cartridge screen, and wherein power is provided by the battery, which is a replaceable and rechargeable battery.

10. The synchronized medication tracking system according to claim 8, wherein the tube spring is a spiral tube spring and is used to ensure the one-by-one extraction of medicines in the tube from the tube placed in the tube area one by one according to a dosage, with a rotation taken from the motor, the tube spring, extracts a tablet placed between spirals from the tube, one tablet in each rotation, and the medicine outlet cover opens and allows the medicine to exit from the medicine outlet.

11. The synchronized medication tracking system according to claim 8, wherein a process of a tablet exiting from the tube is performed by applying a flexible material on an inner surface of the tube, which will be mutually applied to upper and lower sides, with small plies spaced apart there between, the tablets placed between wings on the flexible material move with a movement of a tape, one tablet at a time, when the wings are on a side of a surface of the tube, the wings are bent between the inner surface of the tube and the tape to enable movement of the tape.

12. The synchronized medication tracking system of claim 1, configured to provide accurate, regular and medication usage to a patient by specifying a day, a time, an empty/full stomach state for administration of medication using a time-calendar application and can be synchronized with a mobile application of a patient and a patient's relative, when it is time for the medication to be taken by the patient, both the cartridge gives an audible and visual warning and the mobile application sounds an alarm and the patient is warned by a double alarm method, if the patient does not hear or ignore the warnings, the mobile application sends a warning message to the patient's relatives and informs them.

* * * * *